United States Patent [19]
Stüssi

[11] Patent Number: 5,882,303
[45] Date of Patent: Mar. 16, 1999

[54] PROCESS AND ARRANGEMENT FOR DETERMINING THE DISPERSION PROPERTIES OF MECHANICAL WAVES IN A THREE-DIMENSIONAL OBJECT

[76] Inventor: Edgar Stüssi, Querstrasse 9, CH-8964, Rudolfstetten, Switzerland

[21] Appl. No.: 894,018

[22] PCT Filed: Jan. 25, 1996

[86] PCT No.: PCT/CH96/00034

§ 371 Date: Jul. 23, 1997

§ 102(e) Date: Jul. 23, 1997

[87] PCT Pub. No.: WO96/22732

PCT Pub. Date: Aug. 1, 1996

[30] Foreign Application Priority Data

Jan. 25, 1995 [CH] Switzerland ................. 198/95

[51] Int. Cl.[6] .................................................. A61B 8/00
[52] U.S. Cl. ........................................................ 600/407
[58] Field of Search .................................. 600/407, 437, 600/443, 462; 73/865–865.4, 702–704

[56] References Cited

U.S. PATENT DOCUMENTS 4,913,157  4/1990  Pratt, Jr. et al. ................. 600/449
5,143,069  9/1992  Kwon et al. .

FOREIGN PATENT DOCUMENTS 1249664  1/1989  Canada .

A20306110  3/1989  European Pat. Off. .

OTHER PUBLICATIONS

E. Stussi and D. Fah, "Assessment of bone mineral content by in vivo measurement of flexural wave velocities", Medical & Biological Engineering & Computing, 26 Jul. 1988, vol. 26, No. 4, pp. 349–354.

D. Fah and E. Stussi, "Phase velocity measurement of flexural waves in human tibia", Journal of Biomechanics, 5 Apr. 1988, vol. 21, no. 11, pp. 975–983.

Primary Examiner—Marvin M. Lateef
Assistant Examiner—Ali Imam

[57] ABSTRACT

The process of the invention serves for determining the dispersion properties of mechanical waves in a beam or tube-like object. For this purpose, first, flexural waves are excited in object. These excited flexural waves are calculated in the object longitudinal direction at set distances from each other. The transmission function of the waves is calculated from these calculated values. The flexural waves are generated by means of continuous hammering impulses, wherein the pulse form, particularly the pulse width and pulse height, are automatically set in such a manner that a difference between a theoretic dispersion relation and a value calculated from the known measured values becomes minimal. The rigidity of the object (20), for example a live bone, can be calculated by evaluating the transmission function.

14 Claims, 1 Drawing Sheet

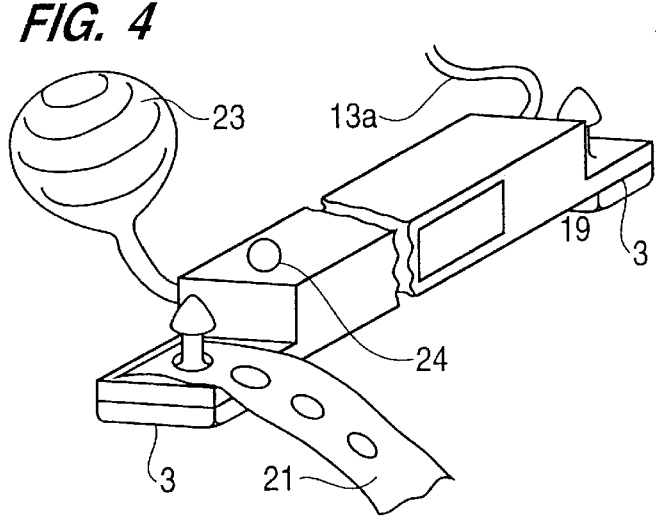
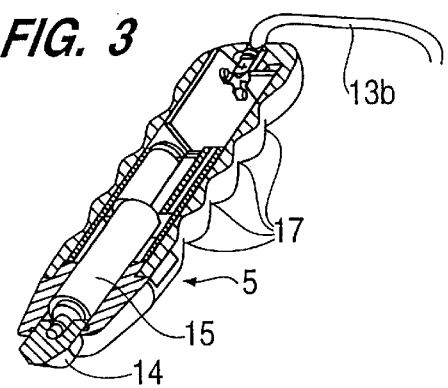
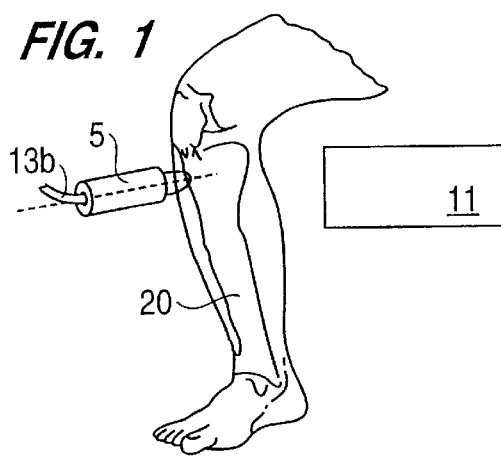
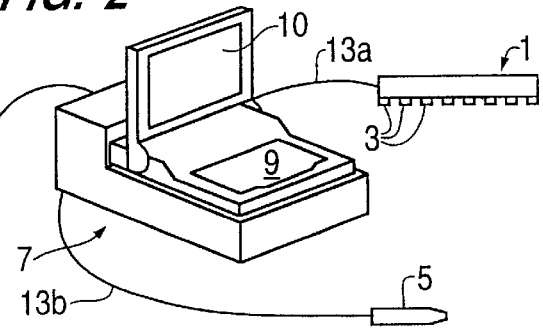
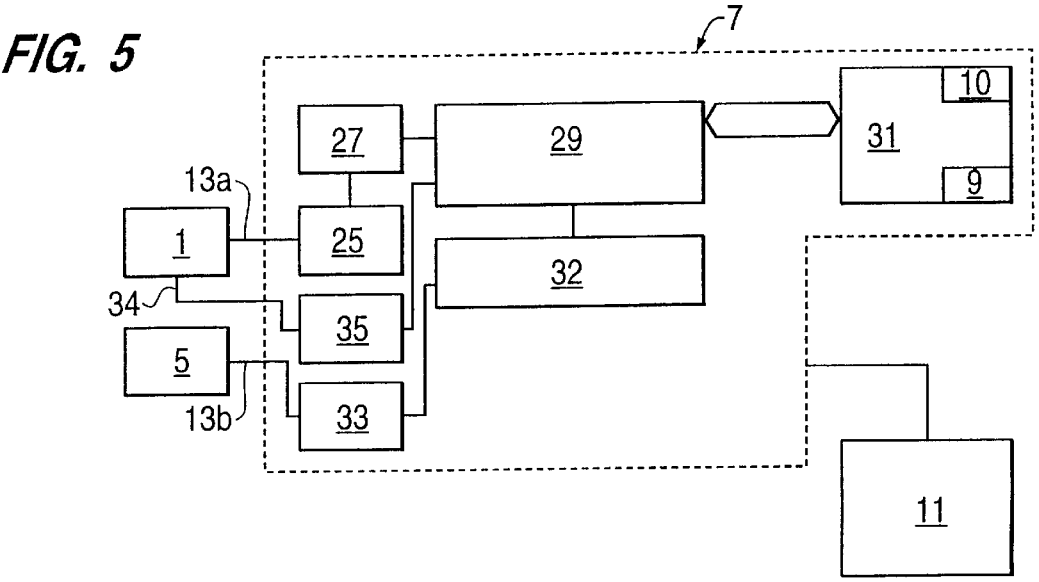

PROCESS AND ARRANGEMENT FOR DETERMINING THE DISPERSION PROPERTIES OF MECHANICAL WAVES IN A THREE-DIMENSIONAL OBJECT

The invention concerns a process according to the generic term of patent claim 1, an arrangement according to patent claim 7, a hammer unit according to the generic term of patent claim 9, a vibration absorption unit according to patent claim 11, an evaluation unit according to patent claim 12, and a control unit according to claim 13.

The rigidity, particularly the rigidity with respect to mechanical torsion of preferred beam or tube-like objects, can be determined relatively easily on the basis of their measurements and materials according to the laws of static. There are, however, certain cases wherein the measurements and/or the exact material composition and density cannot be determined, and the rigidity cannot be calculated. This is the case, on the one hand, in technical objects that cannot be separated or are very hard to separate from the surrounding material and, on the other hand, with live bones which are surrounded by (live) tissue.

The dispersion velocity and attenuation of mechanical waves in beam and tube-like objects stands in direct connection with their surface inertia momentum and with the electricity module of the object material. Based on the publications of [1] E. Stüssi et al., "Assessment of Bone Material Content by In Vivo Measurement of Flexural Wave Velocities," Medical & Biological Engineering & Computing, July 1988, pages 349–354, and [2] D. Fäh et al., "Phase Velocity Measurement of Flexural Waves in Human Tibia," Journal of Biomechanics, Vol. 21, No. 11, pages 975–983, 1988, Great Britain, it is possible to determine the rigidity with respect to torsion by determining the phase velocity of flexural waves dispersing inside the object. The equations (1) and (2) as well as the second equation on page 351 of publication [1] should be particularly taken into consideration for the phase velocities dependent upon the wave lengths. The rigidity of three-dimensional objects can be calculated from the transmission function of the mechanical waves dispersing within the object. This calculation is based, for example, on the models of Bernoulli-Euler, Pochhammer, and Timoshenko . . . as they are referred to in [1] and [2].

If a force impulse is applied to the surface of the object, for example, a shin bone (tibia), then mechanic vibrations are excited within the object. Longitudinal vibrations as well as torsion and flexural vibrations and oscillations are excited and disperse into the ground mode and in higher modes in a beam or tube-like object (tibia). If the resistance to torsion of the shin bone (tibia) is to be determined, a hammer of a hammer unit is applied at about the height of the condyle of the shin bone in the direction of the main inertia axes, approximately vertical to the surface as represented in FIG. 1. The measurement of the excited flexural vibration occurs with the aid of at least two vibration absorption elements distanced from each other longitudinally along the object (tibia). So as to possibly measure only the flexural vibrations on the shin bone (tibia), the excitation point—attack point of the hammer—and both points for vibration measurement are placed in the medio-lateral plane of the diaphysis of the shin bone, that is, approximately parallel to the medial surface of the shin bone. In this configuration, the vibration absorption elements are sensitive only to the direction vertical to the bone surface. The phase velocities for the different flexural vibrations between the vibration absorption elements are determined by means of a numeric evaluation method. The rigidity with respect to torsion can be determined from the length of the beam or tube-like object, its diameter, and the phase velocity of a flexural wave at a certain frequency.

In the known process, a series of measurements must be carried out to obtain a reliable result of the determined wave dispersion properties.

The object of the invention is to determine the wave dispersion properties by means of a process that is fast and easy to apply.

The subject matter of the patent claims is directed toward attaining this object.

The process of the invention is particularly suitable for determining the wave dispersion properties in live bones or in beam or tube-shaped technical objects provided with a coating or imbedded in another material.

The process of the invention is useful for determining the rigidity of the object.

A particularly beam or tube-shaped object is considered in the following as a wave conductor for mechanical waves analog to the hollow conductors in microwaves or glass fibers for optical waves. Such a wave conductor possesses, among others, a dispersion of the phase velocity for the waves lead along by it. That is, the phase velocity of the guided waves, here the mechanical flexural waves, has different values for different wavelengths. As a rule, the value of the phase velocity grows with reducing wavelength. It should be noted, by the way, that the energy transportation takes place with the group velocity of the guided waves.

The phase velocities corresponding to a certain wavelength depend now upon the "wave conducting properties" of the guiding object, here a beam; of course, objects of other shapes can also be used instead of a beam-like object. The more the frequency of the wavelength to be guided comes closer to its limit frequency, the more the value of the phase velocity changes. The limit frequency is the frequency wherein there is still just a wave dispersion with the wave conductor. The value of the limit frequency depends, among others, from the measurements and the material of the wave conductor.

Regarded in themselves, the measurement values do not deliver a diagnosis. The mentioned considerations can be used, however, to determine, from the phase velocity of flexural waves that can be calculated as well as from the changing geometric measurements, which will, in the end, determine the rigidity with respect to torsion: from the value of the phase velocity there can be inferences as to the geometric measurements as well as the material properties and also their changes can be monitored. There is only a passing mention here to the monitoring of corroded pipes, carriers, etc. as well as, in the organic aspect, the determination of osteoporosis and other degrading or changing effects on, for example, the bones.

According to the above considerations, the phase velocity of mechanical flexural waves should preferably be determined in the region of the limit frequency. The work is carried out with the flexural wave arrangement of the invention to obtain the optimum torsion frequency. In this way, a kind of automatic "reverse coupling system" is adapted to the pulse form of a hammer impulse to be applied that excites the flexural wave so that, according to the Fourier analysis or synthesis, the excited flexural waves come to lie in the region of the limit frequency.

Because the excited pulse form of the hammer unit, particularly its pulse width and pulse height, are set automatically so that the deviation of the measured dispersion becomes a theoretically previewed minimum, an automatic cautious approach to a valid pulse form (if possible in the region of the limit frequency) can follow, which is exactly that flexural wave that excites the optimum vibration energy and frequency in the object, and which allows the determination of the parameters described in the above publications for determining the phase velocity of the flexural wave. An optimum frequency band is reached when a dispersion relation comes optimally near to the theoretical values stored in an evaluation unit.

Good results can be achieved as far as a gauss-shaped pulse is applied to the object, since a gauss-shaped pulse also brings with it a gauss-shaped frequency dispersion of the excited frequencies of the flexural vibrations. The gauss-shaped pulse is selected in such a manner that no frequencies are generated that have wave lengths smaller than the diameter of the object. Also, no flexural vibrations should be excited that are greater than the longitudinal measurement of the object. With this requirement, largely longitudinal vibrations as well as torsion vibrations can be avoided. The frequencies "contained" in the gauss-shaped pulse can be determined with the aid of a Fourier analysis.

Since reflections form at the ends of an actual beam-like object during the wave dispersion, the work is carried out advantageously with a "measuring window." The calculation of the optimum window width as well as the positioning in time of the window with respect to the wave excitation by means of the hammer unit occurs in similar manner as in the process for determining the optimum pulse form of the hammer.

The vibration absorption elements of the vibration absorption unit have preferably a adaptable mount. This is particularly advantageous, for example, for determining the wave dispersion in the shin bone, wherein the elements cannot be positioned directly on the bone surface because of the organic tissue that lies in between. By means of the pressure mount, a mechanic impedance adaptation takes place so that an optimum coupling of the mechanic waves of the object can take place on the vibration absorption unit. The pressure mount as well as the data of the vibration absorption unit can be selected so that a filter effect is achieved for measuring the desired waves. These positioning pressure mount can then be set "instinctively" automatically and optimally by means of an easy to use arrangement or, like in the optimization of the hammer impulse or the measuring window, by means of the determined results.

If, instead of two, several vibration absorption elements are installed along the longitudinal direction of the object at a set distance one from the other, then the necessary time for a unmistakable determination of the wave dispersion or rigidity with respect to torsion is largely reduced since, on the one hand, phase jumps appear in the wave dispersion as well as ambiguity and "fading" measuring results can be corrected easier. The individual vibration absorption elements are arranged in a line at a set distance from one another in the vibration absorption unit. The mutual distance must not be the same, but can be such that an ambiguousness of the measuring values can be eliminated.

For carrying out the measuring process, an arrangement is used which consists of one hammer unit, a vibration absorption unit with the vibration absorption elements, a control and evaluation unit. The control and evaluation units is preferably installed together in one single housing. The vibration absorption unit and the hammer unit are preferably separate and connected to this housing by means of a long cable so that they can be measured as independent from the location as possible.

The control and evaluation units are at least partially installed in one of the acceleration absorbers for obtaining a compact unit and at least a partial miniaturization of the electronic unit.

The hammer unit of the invention possesses, in contrast to the ones used previously, no spool with a hammer bolt that accelerates the same, and this allows to set the preferred pulse form of the hammering pulse.

A hammer unit could also, similar to a high-pitched loudspeaker, use a vicarious excitation mechanism.

In the hammer unit as well as in the vibration absorption unit, it can be ensured that particularly when measuring live bones, the areas of positioning of the units can be provided with an exchangeable and/or washable (disinfected) covering to comply with hygienic requirements.

In the following, the examples of the process of the invention as well as a unit necessary for carrying out the process in view of the drawings are explained more in depth. Further advantages of the invention result from the following description text. They show:

FIG. 1 is a sketch for representing the installation of a hammer unit of the arrangement for carrying out the measurement of the rigidity of a beam-like object, here a human shin bone (tibia);

FIG. 2 is a perspective sketch of the arrangement for carrying out the calculation of the rigidity with respect to torsion in a similar beam-like object;

FIG. 3 is a perspective cross-section of the hammer unit contained in the arrangement according to FIG. 2;

FIG. 4 is a perspective representation of the vibration absorption unit used for the arrangement according to FIG. 2; and FIG. 5 is a block circuit diagram of the control and evaluation units integrated into a tabletop computer such as the one represented in FIG. 2.

The arrangement shown in FIG. 2 systematically shows a vibration absorption unit 1 with eight vibration absorption elements 3, a hammer unit 5, as well as an apparatus 7 with a keyboard 9 and a monitor 10. The apparatus 7 is connected to a current supply unit 11 that can be recharged by means of an electric energy storage. The vibration absorption unit 1 and hammer unit 5 are connected to the apparatus 7 via cables 13a and 13b. A data display arrangement (not shown) can also be connected to the apparatus.

The hammer unit 5 represented in cross-section in FIG. 3 has a piezoelectric crystal 15 that operates on a hammering head 14 as hammer giver. The hammering head 14 can be covered by the hood (not shown) that constitutes a hygienic covering. The hammer unit 5 is rod-shaped with gripping rills 17 formed on the surface so that it is easy to grip.

The detailed perspective representation of FIG. 4, which is enlarged with respect to FIG. 2, shows a vibration absorption unit 1 with a holding element 19 on each side for each vibration absorption element 3. A so-called acceleration measurer manufactured by the company Kistler Instruments Inc., type piezotron, for example, can be utilized as vibration absorption element 3. In the positions of the vibration absorption elements 3 is an elastic perforated strip 21 that effects the attachment to the object to be measured. In FIG. 4, a perforated strip 21 is represented in lieu of the vibration absorption element 3 on the left side of the holding element 19. For the purpose of pressing each vibration absorption element 3 with a defined force against the object, the shin bone (tibia) 20 shows below, the vibration absorption elements 3 are pneumatically hammered with a certain pressure. In FIG. 4, the pressure is produced with a hand pump 23, whereby the pressure to be applied is transmitted by means of a settable valve. In a preferred embodiment, a preamplifier (not shown) is provided for amplifying the signals taken from the vibration absorption elements 3.

The apparatus 7 contains an evaluation unit for the signals received by the vibration absorption unit 1 and a control unit for "forming" the hammering impulse of the hammering unit 5 and, if present, for the automatic pressure hammering of the vibration absorption elements 3. In the preferred embodiment represented in FIG. 2, the apparatus 7 is a portable desktop computer with a monitor 10 and keyboard 9, which is integrated into the structural component groups of the control and evaluation units.

The block circuit diagram represented in FIG. 5 shows the main structural component groups. The signals of the eight vibration absorption elements 3 utilized here are transmitted by the vibration absorption unit 1 by means of the cable 13a and are amplified in an eight-channel amplifier as well as filtered out by means of a filter 25 for the evaluation of unnecessary as well as disrupting frequency regions. The measuring window as well as the measuring window opening time are also set by means of the filter 25. The eight signals elaborated in this manner are read into an eight-channel sample-and-hold switch 27, are then digitalized by means of an electric component group 29. They are stored by channel for their further evaluation. According to the embodiments in the above publications [1] and [2], theoretic curve families can be compared in a computer unit 31. A portable minicomputer is preferably used as a computer unit 31. The measuring window width as well as the measuring start are varied according to general error algorithms until a minimum deviation from the theoretic values is reached. The initial signal for the hammer unit 5 is also generated in dependence upon these determined values by means of the computer unit 31, together with a hammering element control switch 32. This signal is amplified, as a rule, only once for driving the piezoelectric crystal 15 in the hammer unit 5 with a driver component group 33 per measured object 20. The pulse form to be generated depends further also from the marginal values entered by means of the keyboard 9 such as, for example, the distances of the vibration absorption elements 3 from each other as well as, for example, the measurable diameter of an approximately tube-shaped object, such as the tibia. The pressure to be optimally transmitted onto the vibration absorption elements 3 is also calculated by the computer unit 31 and is guided to the vibration absorption elements 3 starting at a fluid guide 34 by means of a pressure unit 35 controlled by a computer unit 31.

With the arrangement, it is possible to determine the rigidity with respect to torsion of beam-like objects with different cross sections. That is, complete tube-shaped cross sections can be investigated. The curve families of the phase velocities of the wave dispersion of flexural waves must be easy to store, similar to the embodiments in, for example, the publications [1] and [2] by means of their frequency and in dependence upon the determined marginal requirements. The phase velocity of a flexural wave frequency with the smallest deviation from the theoretically calculated value results in the searched value for rigidity with respect to torsion.

In the example presented herein, the determination of the rigidity with respect to torsion of the tibia is processed with a gauss-shaped hammering impulse, whereby the frequency band is calculated to be between 1 and 10 KHz. Preferably, however, the work is carried out with frequencies between 2 and 5 KHz. The measuring window is opened up to 200 $\mu$s in correspondence with the measurements of the tibia. The measuring values are evaluated in a measuring window of up to 400 $\mu$s. Good results are obtained with a window opening in the region of 300 $\mu$s.

When carrying out the above measurements, it must be especially considered that only the excited flexural waves must be evaluated. The excited wavelengths of the waves should be greater than the transversal dimension and smaller than the longitudinal dimension of the object, as was already explained above.

For reducing the measurement fading, the work is carried out not with single impulses, but with pulse series. These pulse series can contain several identical pulses; the work can also be carried out according to a predetermined pattern of continuously changing pulses.

Instead of arranging the vibration absorption units in series with the hammer unit, a transfer arrangement can also be selected. Also, instead of a hammer brought down vertically onto the surface of the object, the hammer can be brought down at a predetermined angle. The transfer, as well as the inclined direction of the hammer, are then shown if no more flexural waves are utilized for measurement, but the longitudinal vibrations and/or torsion waves are calculated by utilizing other theoretic calculations and models.

With the above-described embodiments, not only can the rigidity of beam-like objects be determined, but also that of objects of any desired cross section. The only requirement is, however, the existence of a theoretic model between the transfer function of the mechanic waves dispersing within the object, and the mechanic properties of this object, particularly rigidity.

The hammering impulse generated in the hammer unit is transmitted by means of the hammering head. The frequencies of the hammering impulse appearing in the analysis according to Fourier selected for the measurement should, if possible, transmit onto the object without an energy loss. If the transmission is to be carried out onto the tibia, then there is unfortunately tissue between the hammering head and the bone surface, which can attenuate the transmitted impulse. A transmission attenuation is the lowest when an optimum application pressure is present. The initially mentioned requirements with respect to a mechanical impedance adaptation are valid also for the hammering head. The optimum application pressure can be determined experimentally. It should be then applied to all the measurements. To maintain the application pressure, the actual pressure must be determined. If the hammering head is made from an electrically conducting material or if it has an electrically conducting surface, then the electric resistance between the hammering head and the organic surface material covering the object (skin) is dependent upon the pressure. This measurement of the electric conductivity allows a defined setting of, for example, the application pressure.

I claim:

1. Process for determining the wave dispersion properties in three dimensions particularly a beam or tube-shaped object (20), wherein the object (20) excites mechanical waves in a first position at locations distanced from each other and wherein the excitation source and transmission function of the waves are determined based on these measured values, characterized in that the waves are generated by a hammering impulse with a pulse form, particularly the pulse width and pulse height, set automatically according to a Fourier synthesis so that the object (20) has excited mechanical waves with sufficient energy of frequency wherein a difference between the theoretic dispersion relationship and a value determined based on the known measurement values is minimal.

2. Process according to claim 1, wherein the rigidity of the object (20) is determined by evaluating the transmission function of the waves.

3. Process according to claim 1, wherein the wave dispersion properties in the live bone are determined, for example, the rigidity of the bone.

4. Process according to one of claim 1, characterized in that each hammering impulse is gauss-shaped and particular pulse series with several preferably identical hammering impulses are applied, whereby preferably the pulse form of the hammering impulse is structured in such a manner for exciting flexural waves in the object (20) that a maximum vibration energy lies in a spectral vibration with a wavelength within the object (20) which is 1.8 to 4.5 times, preferably 2.7 to 3.1 times, greater than the transversal dimension relevant to the vibration.

5. Process according to one of claim 1, characterized in that the phase velocities of the dispersing waves are calculated from the known measurement values and preferably the measurement values are taken up within a predetermined time measurement window with a window width and window opening time that change automatically in dependence upon the difference between the theoretic and the transmission function or rigidity calculated from the measurement values and which are particularly set in such a manner that no wave reflections can be taken up by the limitations of the object (20).

6. Process according to one of claim 1, characterized in that the measurement values are taken up by at least two distanced vibration absorption elements (3), particularly in the object longitudinal direction, having an application pressure against the object, particularly in dependence upon the difference between the theoretic and the transmission function or rigidity calculated from the measurement values, set automatically to carry out, preferably with the excitation of several transmission functions or rigidity measurements, so that particularly the overall measurement time is reduced and eventual phase jumps of the wave dispersion can be corrected, and preferably eliminated.

7. Arrangement for carrying out the process according to one of claim 1, having a hammer unit (5), a vibration absorption unit (1) with at least two vibration absorption elements (3), an evaluation unit (25, 27, 29, 31) connected to an output unit and a control unit (32, 33), wherein the hammer unit (5) is connected to the control unit connected to the evaluation unit and the vibration absorption unit (1) is connected to the evaluation unit to obtain the pulse form, preferably the pulse width and pulse height, of the hammering impulse to be applied onto the object (20) by means of the hammer unit (5) in dependence upon the difference between theoretic transmission functions or rigidity values calculated in the evaluation unit (25, 27, 29, 31) by means of the calculation model of the dispersing waves and for modifying the measurement values calculated by the control unit (32, 33).

8. Arrangement according to claim 7, characterized in that the vibration absorption unit (1) is connected to the control unit (32, 35), particularly by means of the fluid guide (34), so that the application pressure of the vibration absorption elements (3) arranged in the vibration absorption unit (1) against the object (20), particularly in dependence upon the difference to be minimized between a theoretic transmission function or rigidity can be stored in the evaluation unit (25, 27, 29, 31) and calculated from the measurement values.

9. Hammer unit according to claim 7, characterized in that it has preferably piezoelectric hammer givers (15) which are grip-shaped and can be held well in the human hand, which act on the hammering head (14) with an impulse form and energy set by the hammering impulse without causing mechanic changes in the object (20).

10. Hammer unit according to claim 9, characterized in that a pressure measuring unit for determines the application pressure against the object (20) and an application unit with at least three points for position definition with respect to the object (20), and a vibration giver (15) that carries the hammering head (14) which is displaceable in its hammering direction to the surface of the object (20).

11. Vibration absorption unit (1) for utilizing in the arrangement according to claim 7, characterized in that the holding element (19, 21) for receiving the vibration absorption elements and their fixation on the object (20) and a displaceable element that can press each one of the vibration absorption elements (3) against the surface of the object (20) and can be displaced with a settable pressure as well as particularly by means of a membrane, on which fluid is applied, or a piston cylinder unit.

12. Evaluation unit (25, 27, 29, 31) for utilization in the arrangement according to claim 7, with a sample-and-hold and an analog-digital transformer switch unit (27) for the vibration absorption elements (3) of a vibration absorption unit (1).

13. Control unit (32, 35) for utilization in the arrangement according to claim 7, with an electric pulse forming unit (32, 33), with which the pulse width and pulse height of an electric, particularly a tension pulse, for the hammer unit (5) can be automatically set.

14. Control unit (32, 35) according to claim 13, characterized in that a pressure generating unit (35) makes pressure with a predetermined pressure on a pressure means by means of an additional fluid guide (34) at each one of the vibration absorption elements (3) of the arrangement.

* * * * *